United States Patent [19]

Sasaki et al.

[11] Patent Number: 5,208,386

[45] Date of Patent: May 4, 1993

[54] FLUORINE-SUBSTITUTED COMPOUND CONTAINING ETHER BOND

[75] Inventors: Makoto Sasaki, Saitama; Haruyoshi Takatsu; Kiyofumi Takeuchi, both of Tokyo, all of Japan

[73] Assignee: Dainippon Ink and Chemicals, Inc., Tokyo, Japan

[21] Appl. No.: 744,186

[22] Filed: Aug. 9, 1991

[30] Foreign Application Priority Data

Aug. 10, 1990 [JP] Japan .................................. 2-213344
Aug. 10, 1990 [JP] Japan .................................. 2-213345
Aug. 10, 1990 [JP] Japan .................................. 2-213346

[51] Int. Cl.$^5$ .................... C07C 43/166; C07C 43/164
[52] U.S. Cl. ........................................ 568/661; 568/659
[58] Field of Search ................................. 568/659, 661

[56] References Cited

U.S. PATENT DOCUMENTS 4,710,315 12/1987 Schad et al. ..................... 568/660
4,846,998 7/1989 Pohl et al. ....................... 568/659

FOREIGN PATENT DOCUMENTS

0415090A1 3/1991 European Pat. Off. .
3631611A1 4/1988 Fed. Rep. of Germany .
4025419A1 2/1991 Fed. Rep. of Germany .

Primary Examiner—Marianne M. Cintins
Assistant Examiner—Margaret J. Page
Attorney, Agent, or Firm—Armstrong, Westerman, Hattori, McLeland & Naughton

[57] ABSTRACT

A fluorine-substituted compound containing an ether bond is disclosed, which is represented by formula

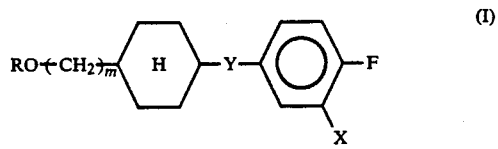

wherein R represents a straight chain alkyl group having from 1 to 5 carbon atoms; m represents an integer of from 1 to 7; X represents hydrogen atom or fluorine atom; Y represents a connecting group selected from a group consisting of

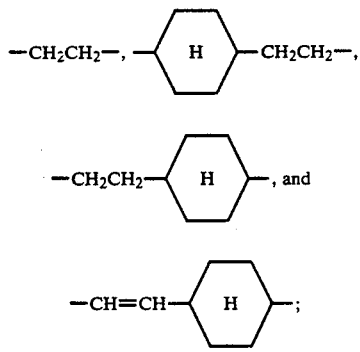

and the cyclohexane ring represents a trans(equatorial-equatorial) cyclohexane ring.

5 Claims, No Drawings

FLUORINE-SUBSTITUTED COMPOUND CONTAINING ETHER BOND

FIELD OF THE INVENTION

The present invention relates to a compound containing an ether bond useful as an electrooptical display material, and more particularly, it relates to a compound containing an ether bond, which effectively lowers the threshold voltage.

BACKGROUND OF THE INVENTION

Typical examples of liquid crystal cell include a field effect mode cell proposed by M. Schadt et al., *Applied Physics Letters*, 18, 127-128 (1971), a dynamic scattering mode cell proposed by G. H. Heilmeir et al., *Proceeding of the I.E.E.E.*, 56, 1162-1171 (1968), and a guest/host mode cell proposed by G. H. Heilmeir et al., *Applied Physics Letters*, 13, 91 (1968) or D. L. White et al., *Journal of Applied Physics*, 45, 4718 (1978).

These liquid crystal display cells are required to satisfy various characteristics, with quick response and low threshold voltage ($V_{th}$) being the most important ones. Liquid crystal display cells having a low threshold voltage can be driven at a low voltage. Quick response liquid crystal display cells, on the other hand, can be fabricated by using liquid crystal materials low in viscosity, since the response time ($\tau$) is directly proportional to the viscosity ($\eta$) of the liquid crystal material, i.e., $\tau \propto \eta$.

Among these liquid crystal display cells mentioned hereinbefore, the TN mode cells which belong to the field effect mode cells, are mainly used at present. In the case of the TN mode cells, it is required to set the product of the optical anisotropy ($\Delta n$) of the liquid crystal material in the cell and the thickness (d)μm of the cell to a definite value in order to achieve good cell appearance, as indicated by G. Bauer, *Mol. Cryst. Liq. Cryst.*, 63, 45 (1981). A liquid crystal display cell used in practice has a Δn·d value selected from among 0.5, 1.0, 1.6, and 2.2. In general, the viewing properties of a liquid crystal display cell can be improved by setting the Δn·d value to 0.5. On the other hand, the frontal contrast thereof can be ameliorated by setting the Δn·d value to 1.0, 1.6, or 2.2. Therefore, it is generally recommended to set the Δn·d value of a liquid crystal display cell to 0.5 when it is considered more important to achieve excellent viewing properties from any direction. On the other hand, the Δn·d value thereof is preferably set to 1.0, 1.6, or 2.2 to obtain a clear frontal contrast.

However, the thickness in a liquid crystal display cell used in practice is commonly set to a definite value within a limited range of from 6 to 10 μm. Thus, a liquid crystal material having a low Δn is required to set the Δn·d value to 0.5. In contrast thereto, a liquid crystal material having a high Δn value is requisite to obtain a Δn·d value of 1.0, 1.6, or 2.2. That is, either a liquid crystal material of a low Δn value or one of a high Δn value is required depending on the desired display properties.

In the TN mode cells, the dielectric anisotropy (Δε) of a mixed liquid crystal is required to be positive. Therefore, it is demanded to provide nematic liquid crystal materials which are large in Δε value and low in threshold voltage, hence capable of being driven at a low voltage.

As a viscosity depressant known to the present to use for the purposes mentioned hereinbefore, mentioned is a compound represented by formula (a) below

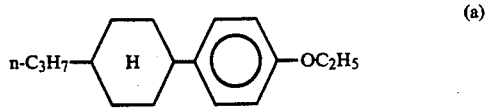

(a)

However, the compound represented by formula (a) above suffers a disadvantage, since the addition of this compound to a liquid crystal matrix commonly used at present as the nematic liquid crystal composition reduces the viscosity of the liquid crystal matrix at one hand, and increases the threshold voltage on the other.

SUMMARY OF THE INVENTION

An object of the present invention is to provide a novel nematic liquid crystal compound having a low Δn value and a large Δε, which, upon addition thereof to a liquid crystal matrix, effectively lowers the viscosity and the threshold voltage of said liquid crystal matrix.

The object of the present invention was achieved by a compound represented by formula (I):

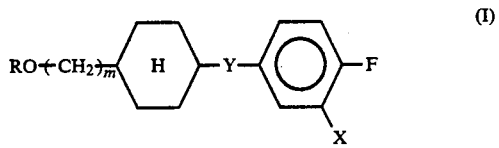

(I)

wherein R represents a straight chain alkyl group having from 1 to 5 carbon atoms; m represents an integer of from 1 to 7; X represents hydrogen atom or fluorine atom; Y represents a connecting group selected from a group consisting of

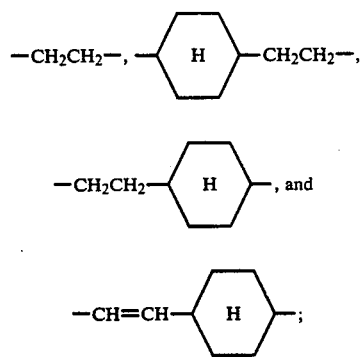

and the cyclohexane ring represents a trans(equatorial-equatorial) cyclohexane ring.

The compound represented by formula (I) according to the present invention can be produced by a process shown below.

(1) With Y being 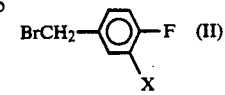—CH$_2$CH$_2$—:

BrCH$_2$—⟨○⟩—F  (II)

|
  X

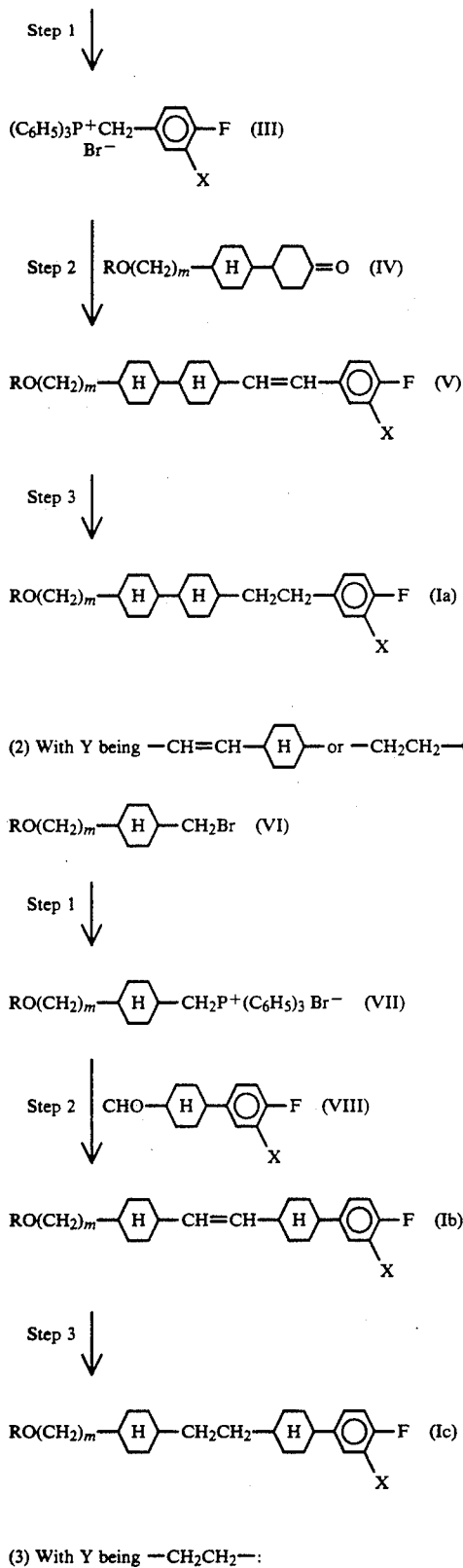

(2) With Y being —CH=CH—⟨H⟩— or —CH₂CH₂—⟨H⟩—:

(3) With Y being —CH₂CH₂—:

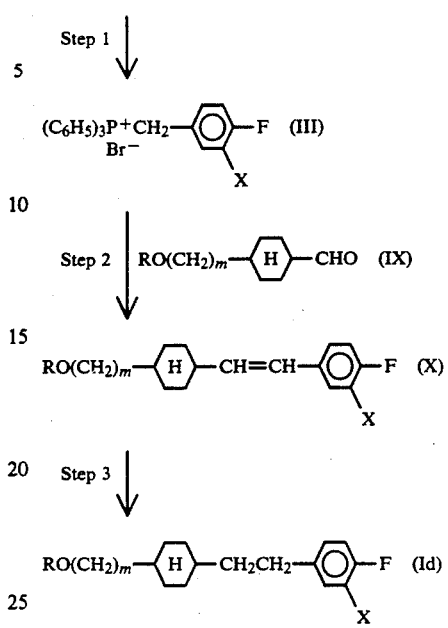

In the reaction processes above, R represents a straight chain alkyl group having from 1 to 5 carbon atoms; m represents an integer of from 1 to 7; X represents hydrogen atom or fluorine atom; and the cyclohexane ring represents a trans(equatorial-equatorial) cyclohexane ring.

In the reaction scheme (1), the reaction at each step is as follows:

Step 1

A compound of formula (II) is reacted with triphenylphosphine in toluene to obtain the compound represented by formula (III).

Step 2

The compound of formula (III) is treated with a strong base such as potassium t-butoxide in tetrahydrofuran to obtain a Wittig reagent, and then reacted with a compound represented by formula (IV) to obtain a compound represented by formula (V).

Step 3

The compound of formula (V) is catalytically reduced in ethyl acetate using Raney nickel as the catalyst to obtain a compound represented by formula (Ia) which belongs to the compound of the present invention represented by formula (I).

In the reaction schemes (2) and (3), similar reactions take place; compounds represented by formulae (Ib), (Ic), and (Id), all belonging to the compound represented by formula (I), can be obtained analogously.

The phase transition temperature for each of the representative compounds represented by formula (I) is given in Table 1.

TABLE 1
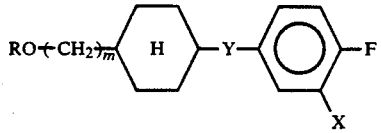
| No. | R | m | Y | X | Phase transition temperature (°C.) |
|---|---|---|---|---|---|
| 1 | CH₃— | 2 | H—◯—CH₂CH₂— | F | 42 (C → N); 89 (N ⇄ I) |
| 2 | CH₃— | 3 | H—◯—CH₂CH₂— | H | 56 (C → S); 92 (S ⇄ N); 150 (N ⇄ I) |
| 3 | CH₃— | 3 | H—◯—CH₂CH₂— | F | 49 (C → S); 70 (S ⇄ N); 107 (N ⇄ I) |
| 4 | CH₃— | 5 | H—◯—CH₂CH₂— | H | 68 (C → S); 107 (S ⇄ N); 149 (N ⇄ I) |
| 5 | CH₃— | 5 | H—◯—CH₂CH₂— | F | 44 (C → S); 69 (S ⇄ N); 105 (N ⇄ I) |
| 6 | CH₃— | 2 | —CH=CH—◯— | F | 45 (C → N); 91 (N ⇄ I) |
| 7 | CH₃— | 3 | —CH=CH—◯— | H | 81 (C → N); 159 (N ⇄ I) |
| 8 | CH₃— | 3 | —CH=CH—◯— | F | 58 (C → N); 123 (N ⇄ I) |
| 9 | CH₃— | 5 | —CH=CH—◯— | F | 51 (C → N); 124 (N ⇄ I) |
| 10 | CH₃— | 2 | —CH₂CH₂—◯— | F | 37 (C → N); 72 (N ⇄ I) |

TABLE 1-continued

RO—(CH₂)ₘ—⟨H⟩—Y—⟨○⟩—F with X substituent

| No. | R | m | Y | X | Phase transition temperature (°C) |
|-----|---|---|---|---|-----------------------------------|
| 11 | CH₃— | 3 | —CH₂CH₂—⟨H⟩— | H | 58 (C ⇌ N); 137 (N ⇌ I) |
| 12 | CH₃— | 3 | —CH₂CH₂—⟨H⟩— | F | 53 (C ⇌ N); 95 (N ⇌ I) |
| 13 | CH₃— | 5 | —CH₂CH₂—⟨H⟩— | F | S phase at room temperature; 45 (S ⇌ N); 96 (N ⇌ I) |
| 14 | CH₃— | 3 | —CH₂CH₂— | F | 20 (melting point) |
| 15 | CH₃— | 5 | —CH₂CH₂— | H | 51 (melting point) |
| 16 | CH₃— | 5 | —CH₂CH₂— | F | 35 (melting point) |

In Table 1, C represents a crystalline phase, S represents a smectic phase, N represents a nematic phase, and I represents an isotropic liquid phase.

The compounds Nos. 1 to 13 in Table 1, which are all compounds represented by formula (I) according to the present invention, are nematic liquid crystal compounds having a positive dielectric anisotropy. Thus, for example, they may be mixed with other nematic liquid crystal compounds having a negative dielectric anisotropy and applied to a dynamic scattering mode display cell material. Alternatively, they may be mixed with other nematic liquid crystal compounds having a negative or positive dielectric anisotropy and applied to a field effect mode display cell material.

The compounds Nos. 14 to 16 in Table 1, which are all also compounds represented by formula (I) according to the present invention, are not nematic. However, they may be similarly used, for example, as mixtures with other nematic liquid crystal compounds having either a positive or negative dielectric anisotropy and used as a field effect mode display cell material.

Typical examples of the compounds which can be preferably mixed with the compound of formula (I) include, 4-substituted benzoic acid 4'-substituted phenyl esters, 4-substituted cyclohexanecarboxylic acid 4'-substituted phenyl esters, 4-substituted cyclohexanecarboxylic acid 4'-substituted biphenyl esters, 4-(4-substituted cyclohexanecarbonyloxy) benzoic acid 4'-substituted phenyl esters, 4-(4-substituted cyclohexyl) benzoic acid 4'-substituted cyclohexyl esters, 4-substituted 4'-substituted biphenyls, 4-substituted phenyl-4'-substituted cyclohexanes, 4-substituted 4"-substituted terphenyls, 4-substituted biphenyl 4'-substituted cyclohexanes, and 2-(4-substituted phenyl)-5-substituted pyrimidines.

When added to a commonly used liquid crystal matrix as a nematic liquid crystal material, the compounds represented by formula (I) according to the present invention are excellent in that they lower the threshold voltage of the liquid crystal composition without substantially increasing the viscosity of the composition. Among the compounds represented by formula (I), the bicyclic compounds having —CH₂CH₂— as Y have a particularly pronounced effect in lowering the viscosity of the liquid crystal composition.

Table 2 shows measured viscosity (centipoise, cP) at 20° C. and threshold voltage (V$_{th}$) of each liquid crystal mixture comprising 90% by weight of a matrix liquid crystal (A) which is widely employed as a nematic liquid crystal material having an excellent multiplexibility, and 10% by weight of any of the compounds of formula (I), No. 14, No. 15, or No. 16; or, for comparison, of a compound of formula (a) below which is generally employed as an effective viscosity depressant; or of a compound of formula (b) below which has a structure similar to the compound No. 14.

The matrix liquid crystal (A) comprises:

40% by weight of

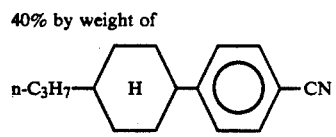

30% by weight of

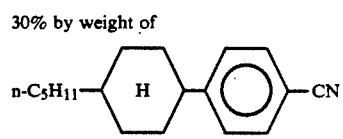

and

-continued

30% by weight of

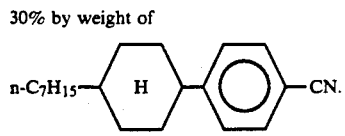

The compounds (a) and (b) are each represented by the following formula.

(a)
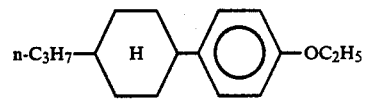

(b)
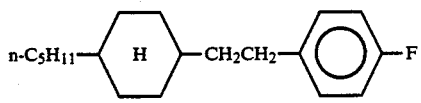

TABLE 2

| Liquid Crystal Mixture | Viscosity (cP/20° C.) | Threshold Voltage (V) |
|---|---|---|
| (A) | 22.0 | 1.51 |
| (A) + No. 14 | 20.9 | 1.15 |
| (A) + No. 15 | 19.8 | 1.25 |
| (A) + No. 16 | 21.5 | 1.16 |
| (A) + (a) | 20.2 | 1.53 |
| (A) + (b) | 20.1 | 1.39 |

It can be seen from Table 2 that the compounds of formula (I) decrease the viscosity of the matrix liquid crystal (A), and also considerably lower the threshold value.

These superiorities are clear with respect to the decrease in the threshold voltage when the compounds of formula (I) are compared with the compound (a) commonly used as a viscosity depressant and with the compound (b) having a structure similar to that of the compound No. 14 according to the present invention.

Table 3 shows measured threshold voltage ($V_{th}$), $\Delta n$, and $\Delta \epsilon$ of each liquid crystal mixture comprising 80% by weight of a nematic liquid crystal (B) which is widely employed as a matrix liquid crystal and 20% by weight of each of the compounds of formula (I), Nos. 1 to 13; or of a compound of formula (c), (d), or (e) below for comparison, which each has a structure similar to the compounds of formula (I) and having a low $\Delta n$ with a positive $\Delta \epsilon$. Also for comparison, the threshold voltage, $\Delta n$, $\Delta \epsilon$ for the liquid crystal composition (B) is given in the Table.

The liquid crystal composition (B) comprises:

20% by weight of

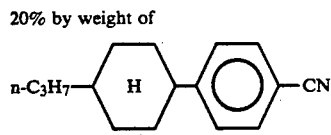

16% by weight of

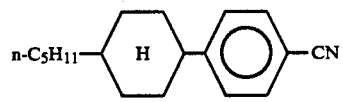

16% by weight of

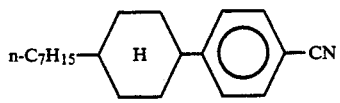

8% by weight each of the following

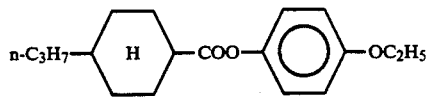

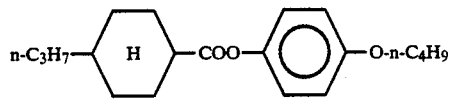

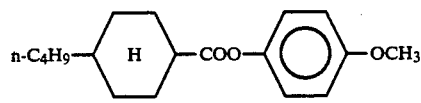

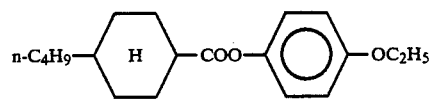

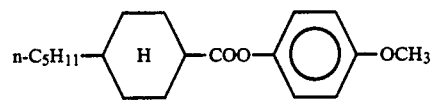

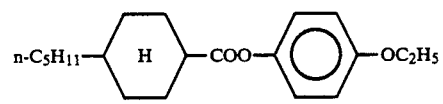

The compounds (c), (d), and (e) for comparison are each represented by formulae below.

(c)
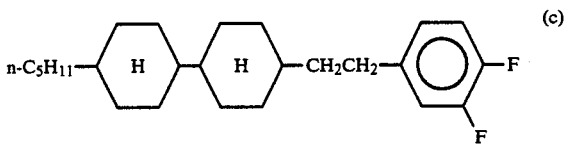

(d)
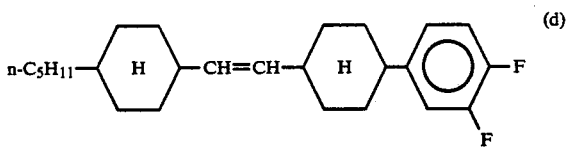

and (e)
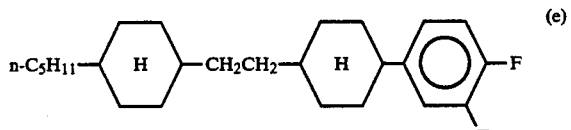

TABLE 3

| Liquid Crystal Mixture | $\Delta n$ | $\Delta \epsilon$ | Threshold Voltage (V) |
|---|---|---|---|
| (B) | 0.092 | 6.7 | 1.60 |
| (B) + No. 1 | 0.091 | 6.9 | 1.50 |
| (B) + No. 2 | 0.096 | 6.8 | 1.69 |
| (B) + No. 3 | 0.091 | 7.1 | 1.50 |
| (B) + No. 4 | 0.095 | 6.8 | 1.69 |

TABLE 3-continued

| Liquid Crystal Mixture | Δn | Δε | Threshold Voltage (V) |
| --- | --- | --- | --- |
| (B) + No. 5 | 0.091 | 7.0 | 1.51 |
| (B) + (c) | 0.096 | 6.3 | 1.91 |
| (B) + No. 6 | 0.092 | 6.9 | 1.50 |
| (B) + No. 7 | 0.096 | 6.7 | 1.70 |
| (B) + No. 8 | 0.092 | 7.1 | 1.51 |
| (B) + No. 9 | 0.092 | 7.0 | 1.51 |
| (B) + No. 10 | 0.091 | 6.9 | 1.50 |
| (B) + No. 11 | 0.095 | 6.7 | 1.69 |
| (B) + No. 12 | 0.091 | 7.0 | 1.52 |
| (B) + No. 13 | 0.091 | 7.0 | 1.52 |
| (B) + (d) | 0.097 | 6.3 | 1.90 |
| (B) + (e) | 0.095 | 6.3 | 1.89 |

It can be seen from Table 3 that the compounds of formula (I) according to the present invention lower Δn, or increase Δε without so much increasing the Δn, or remarkably lower the threshold voltage without so much increasing Δε or Δn, of the mixed liquid crystal. The effect of the present invention is apparent, by comparing the results obtained for the compound No. 3 according to the present invention with that of the conventionally known compound of formula (c) having a structure similar to that of the compound No. 3, those for the compound No. 8 according to the present invention with that of the conventionally known compound of formula (d) having a structure similar to that of the compound No. 8, or by comparing those for the compound No. 12 according to the present invention with that of the conventionally known compound of formula (e) having a structure similar to that of the compound No. 12. That is, the compounds according to the present invention sufficiently lower the threshold value as well as the Δn value while increasing the Δε, whereas the compounds (c), (d), and (e) yield practically unfavorable effects, i.e., they considerably increase the threshold voltage of the mixed liquid crystal as well as the Δn value while decreasing the Δε.

The compounds represented by formula (I) according to the present invention have excellent solubility with respect to the matrix liquid crystal widely used in practice as nematic liquid crystal compositions, and, when they are added therein, they can effectively lower the viscosity of the liquid crystal composition as well as the threshold voltage. Particularly among them, the compounds of three ring systems represented by formula (I) according to the present invention have further superior effects in lowering the Δn and increasing the Δε of the resulting liquid crystal composition.

Thus, the compounds represented by formula (I) according to the present invention are particularly useful for fabricating TN mode liquid crystal display cells which provide quick response, low voltage drive, and excellent viewing properties.

The present invention is illustrated in further detail by referring to some examples below, but it should be understood that the present invention is not to be construed as being limited thereto.

EXAMPLE 1

(1-a)

To 200 ml of toluene was added 20.7 g (0.1 mole) of

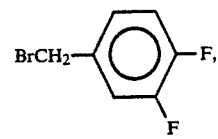

and after adding thereto 26.3 g (0.1 mole) of triphenylphosphine, the resulting solution was heated under refluxing for 3 hours. The crystal obtained upon cooling the solution was filtered off and vacuum dried to obtain 45.1 g (0.096 mole) of compound represented by

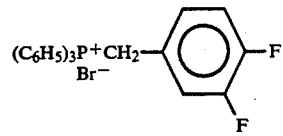

The compound (45.1 g, 0.096 mole) thus obtained was added to 250 ml of tetrahydrofuran, cooled to −5° C., treated with 12.9 g (0.12 mole) of potassium t-butoxide, and allowed to react at room temperature for 1 hour. The reaction mixture was then cooled to −5° C., followed by adding dropwise thereto 80 ml of a dry tetrahydrofuran solution containing 21.3 g (0.08 mole) of compound represented by

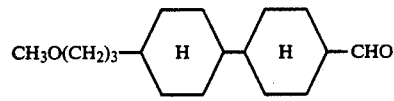

to effect the reaction at room temperature for 2 hours. Upon completion of the reaction, 250 ml of water was added to the reaction product, and the resulting product was extracted thrice with 150 ml of ethyl acetate. The extract was washed with water and dried, and the residue obtained by distilling off the solvent under reduced pressure was dissolved into 100 ml of toluene. To this toluene solution was further added a same amount of hexane to obtain precipitates of triphenylphosphine oxide. The residue obtained by condensing the filtrate under reduced pressure was purified by chromatography on a silica gel column to obtain 24.5 g (0.065 mole) of the following compound:

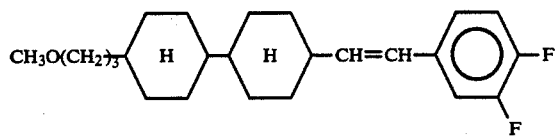

(1-b)

The compound (24.5 g, 0.065 mole) thus obtained was dissolved in 250 ml of ethyl acetate and subjected to catalytic reduction at 50° C. for 6 hours under a hydrogen pressure of 5 kg/cm², using 3 g of Raney nickel as the catalyst. After separating the catalyst by filtration, the filtrate was condensed under reduced pressure to obtain a residue which was recrystallized from ethanol for purification. Thus was obtained 20.7 g (0.055 mole). of the compound shown below, which corresponds to the compound No. 3 in Table 1.

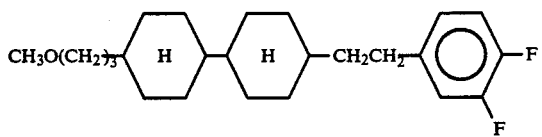

Transition temperature: 49° C. (C→S), 70° C. (S⇌N), 107° C. (N⇌I).

EXAMPLE 2

The same procedure as in Example 1 was followed, except for using 20.2 g (0.08 mole) of the compound below

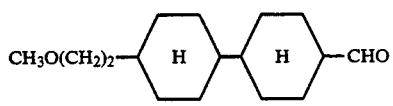

in the place of

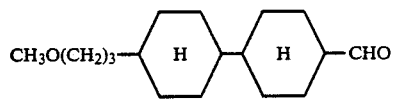

of Example 1, to thereby obtain the compound shown below, which corresponds to the compound No. 1 in Table 1.

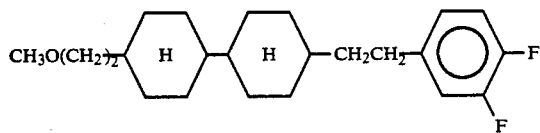

Transition temperature: 42° C. (C→N), 89° C. (N⇌I).

EXAMPLE 3

The same procedure as in Example 1 was followed, except for using 18.7 g (0.1 mole) of the compound below

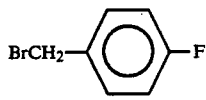

in the place of

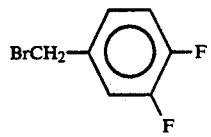

of Example 1, to thereby obtain the compound shown below, which corresponds to the compound No. 2 in Table 1.

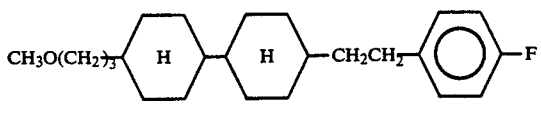

Transition temperature: 56° C. (C→S), 92° C. (S⇌N), 150° C. (N⇌I).

EXAMPLE 4

The same procedure as in Example 1 was followed, except for using 23.5 g (0.08 mole) of the compound below

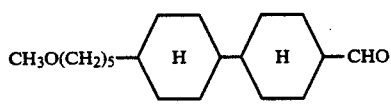

in the place of

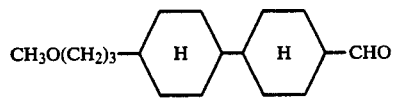

of Example 1, and 18.7 g (0.1 mole) of the compound below

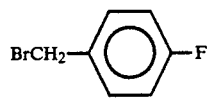

in the place of

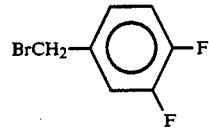

of Example 1, to thereby obtain the compound shown below, which corresponds to the compound No. 4 in Table 1.

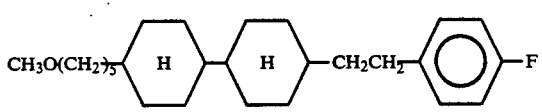

Transition temperature: 68° C. (C→S), 107° C. (S⇌N), 149° C. (N⇌I).

EXAMPLE 5

The same procedure as in Example 1 was followed, except for using 23.5 g (0.08 mole) of the compound below

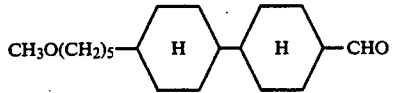

in the place of

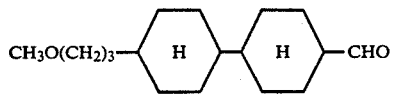

of Example 1, to thereby obtain the compound shown below, which corresponds to the compound No. 5 in Table 1.

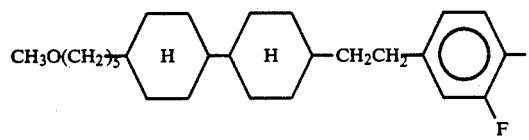

Transition temperature: 44° C. (C→S), 69° C. (S⇌N), 105° C. (N⇌I).

EXAMPLE 6

The same procedure as in Example (1-a) was followed, except for using 24.9 g (0.1 mole) of the compound below

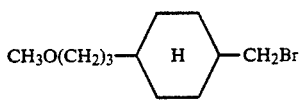

in the place of

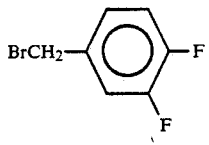

of Example (1-a), to thereby obtain the compound shown below, which corresponds to the compound No. 8 in Table 1.

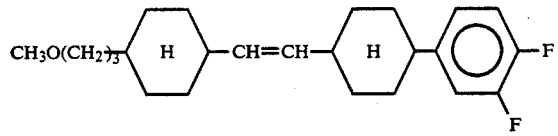

Transition temperature: 58° C. (C→N), 123° C. (N⇌I).

EXAMPLE 7

The same procedure as in Example (1-b) was followed, except for using 24.5 g (0.065 mole) of the compound obtained in Example 6 above,

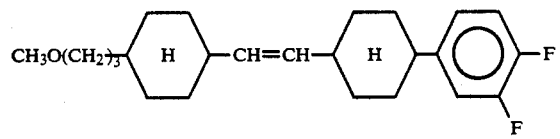

in the place of

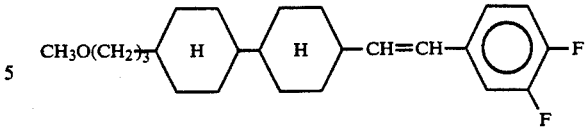

of the compound obtained in Example (1-a), to thereby obtain the compound shown below, which corresponds to the compound No. 12 in Table 1.

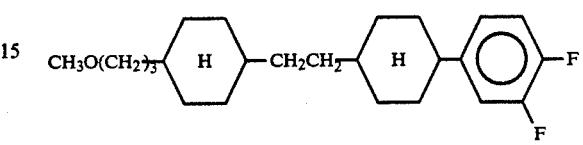

Transition temperature: 53° C. (C→N), 95° C. (N⇌I).

EXAMPLE 8

The same procedure as in Example (1-a) was followed, except for using 23.5 g (0.1 mole) of the compound below

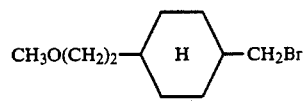

in the place of

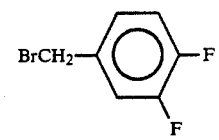

of Example (1-a), to thereby obtain the compound shown below, which corresponds to the compound No. 6 in Table 1.

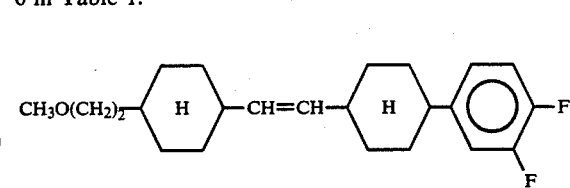

Transition temperature: 45° C. (C→N), 91° C. (N⇌I).

EXAMPLE 9

The same procedure as in Example (1-b) was followed, except for using the compound below obtained in Example 8

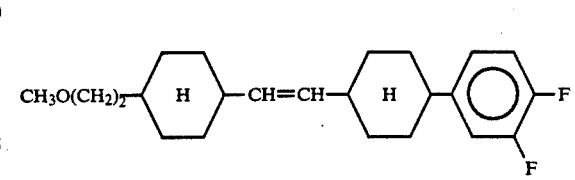

in the place of

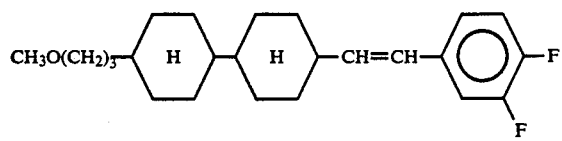

obtained in Example (1-a), to thereby obtain the compound shown below, which corresponds to the compound No. 10 in Table 1.

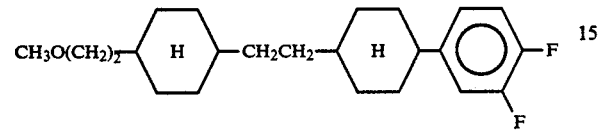

Transition temperature: 37° C. (C→N), 72° C. (N⇌I).

EXAMPLE 10

The same procedure as in Example (1-a) was followed, except for using 16.5 g (0.08 mole) of the compound below

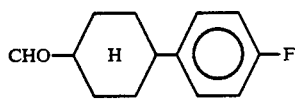

in the place of

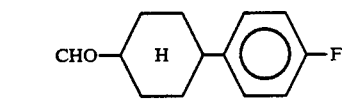

of Example (1-a), to thereby obtain the compound shown below, which corresponds to the compound No. 7 in Table 1.

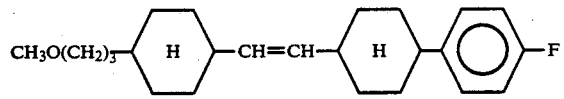

Transition temperature: 81° C. (C→N), 159° C. (N⇌I),

EXAMPLE 11

The same procedure as in Example (1-b) was followed, except for using the compound below obtained in Example 10

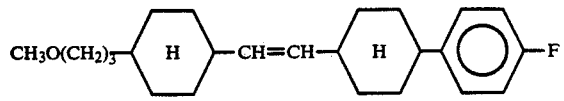

in the place of the compound obtained in Example (1-a), to thereby obtain the compound shown below, which corresponds to the compound No. 11 in Table 1.

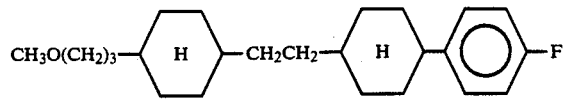

Transition temperature: 58° C. (C→N), 137° C. (N⇌I).

EXAMPLE 12

The same procedure as in Example (1-a) was followed, except for using 27.7 g (0.1 mole) of the compound below

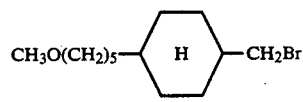

in the place of

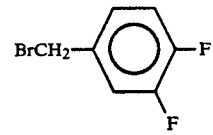

of Example (1-a), to thereby obtain the compound shown below, which corresponds to the compound No. 9 in Table 1.

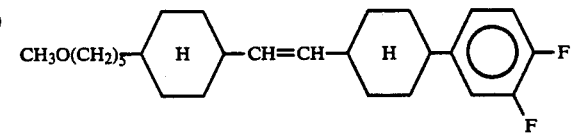

Transition temperature: 51° C. (C→N), 124° C. (N⇌I).

EXAMPLE 13

The same procedure as in Example (1-b) was followed, except for using the compound below obtained in Example 12 above

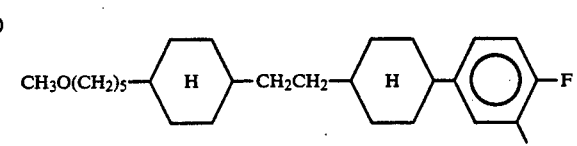

in the place of the compound obtained in Example (1-a) to thereby obtain the compound shown below, which corresponds to the compound No. 13 in Table 1.

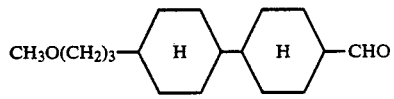

Transition temperature: Room temperature or below (C→S), 45° C. (S→N), 96° C. (N→I).

EXAMPLE 14

The same procedure as in Example 1 was followed, except for using 14.7 g (0.08 mole) of the compound below

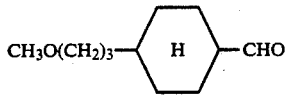

in the place of

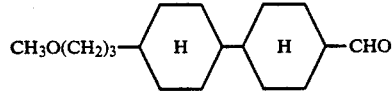

of Example 1, to thereby obtain the compound shown below, which corresponds to the compound No. 14 in Table 1.

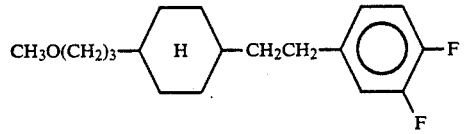

Melting point: 20° C.

EXAMPLE 15

The same procedure as in Example 1 was followed, except for using 17.0 g (0.08 mole) of the compound below

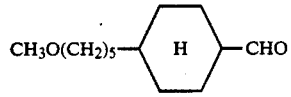

in the place of

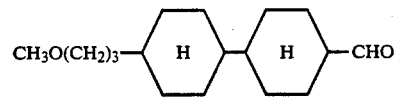

of Example 1, to thereby obtain the compound shown below, which corresponds to the compound No. 16 in Table 1.

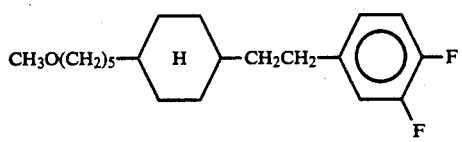

Melting point: 35° C.

EXAMPLE 16

The same procedure as in Example 1 was followed, except for using 18.7 g (0.1 mole) of the compound below

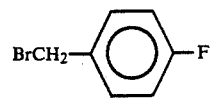

in the place of

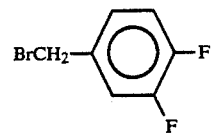

of Example 1, and 17.0 g (0.08 mole) of the compound below

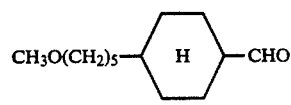

in the place of

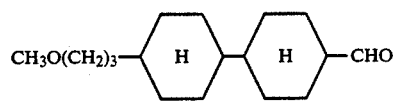

of Example 1, to thereby obtain the compound shown below, which corresponds to the compound No. 15 in Table 1.

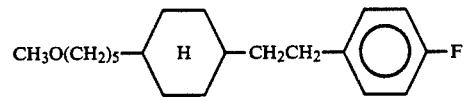

Melting point: 51° C.

While the invention has been described in detail and with reference to specific embodiments thereof, it will be apparent to one skilled in the art that various changes and modifications can be made therein without departing from the spirit and scope thereof.

What is claimed is:

1. A compound represented by formula (I):

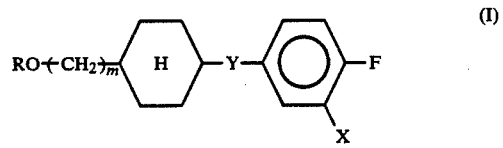

(I)

wherein R represents a straight chain alkyl group having from 1 to 5 carbon atoms; m represents an integer of from 1 to 7; X represents hydrogen atom or fluorine atom; Y represents a connecting group selected from a consisting of

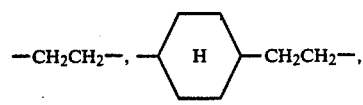

-continued
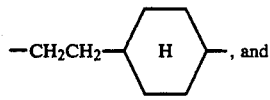, and
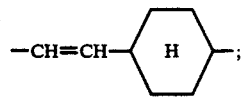;
and the cyclohexane ring represents a trans(equatorial-equatorial) cyclohexane ring.
2. A compound as claimed in claim 1, wherein Y is —CH$_2$CH$_2$—.
3. A compound as claimed in claim 1, wherein Y is
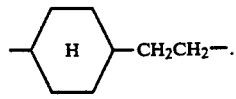.
4. A compound as claimed in claim 1, wherein Y is
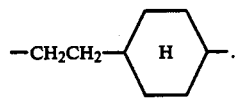.
5. A compound as claimed in claim 1, wherein Y is
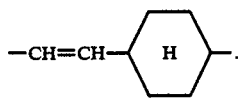.
* * * * *